(12) United States Patent
Shkolnikov et al.

(10) Patent No.: US 11,230,692 B2
(45) Date of Patent: Jan. 25, 2022

(54) PARTICLE SEPARATION AND ANALYSIS

(71) Applicant: HEWLETT-PACKARD DEVELOPMENT COMPANY, L.P., Spring, TX (US)

(72) Inventors: Viktor Shkolnikov, Palo Alto, CA (US); Alexander Govyadinov, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 16/605,985

(22) PCT Filed: Mar. 27, 2018

(86) PCT No.: PCT/US2018/024669
§ 371 (c)(1),
(2) Date: Oct. 17, 2019

(87) PCT Pub. No.: WO2019/190489
PCT Pub. Date: Oct. 3, 2019

(65) Prior Publication Data
US 2021/0277350 A1    Sep. 9, 2021

(51) Int. Cl.
*C12M 1/00*      (2006.01)
*G01N 33/543*    (2006.01)
*G01N 33/569*    (2006.01)

(52) U.S. Cl.
CPC ............ *C12M 47/04* (2013.01); *C12M 47/06* (2013.01); *G01N 33/54366* (2013.01); *G01N 33/569* (2013.01)

(58) Field of Classification Search
CPC ..... B01L 2200/0652; B01L 2300/0816; B01L 2300/0864; B01L 2400/0439;
(Continued)

(56) References Cited

U.S. PATENT DOCUMENTS

| 2018/0038876 A1 | 2/2018 | Arai | |
| 2018/0056294 A1* | 3/2018 | Di Carlo | G01N 33/54333 |
| 2018/0080060 A1* | 3/2018 | Gifford | G01N 15/1056 |

FOREIGN PATENT DOCUMENTS

| CA | 2844056 A1 | 2/2013 |
| CA | 2892490 A1 | 5/2014 |

(Continued)

*Primary Examiner* — Jennifer Wecker
(74) *Attorney, Agent, or Firm* — HP Inc. Patent Department

(57) ABSTRACT

An example system includes an input channel to receive particles through a first end, a separation chamber, at least two output channels, an integrated pump to facilitate flow through the separation chamber and a cell analysis portion. The separation chamber is in fluid communication with a second end of the input channel. The separation chamber has a passive separation structure including an array of columns spaced apart to facilitate separation of particles into at least two flow paths based on a size of the particles. The size associated with a first flow path of the at least two flow paths corresponds to a cell. A first output channel is to receive the first flow path corresponding to a cell. The cell analysis portion is coupled to the first output channel and is to perform at least one analysis associated with cells in the first output channel.

15 Claims, 6 Drawing Sheets

(58) Field of Classification Search
CPC ..... B01L 2400/0442; B01L 2400/0487; B01L 2400/086; B01L 3/502715; B01L 3/502761; G01N 1/4077; G01N 15/02; G01N 15/1056; G01N 15/1484; G01N 2015/0288; G01N 2015/1006; G01N 2015/1081; G01N 2015/1087; G01N 2015/149; G01N 2015/1493

See application file for complete search history.

(56) References Cited

FOREIGN PATENT DOCUMENTS

| | | |
|---|---|---|
| CN | 106754344 B | 11/2017 |
| WO | WO2014145152 A2 | 9/2014 |
| WO | WO2016175843 A1 | 11/2016 |
| WO | WO2017018977 A1 | 2/2017 |
| WO | WO2017035262 A1 | 3/2017 |
| WO | WO2017091213 A1 | 6/2017 |
| WO | WO2017119902 A1 | 7/2017 |

\* cited by examiner

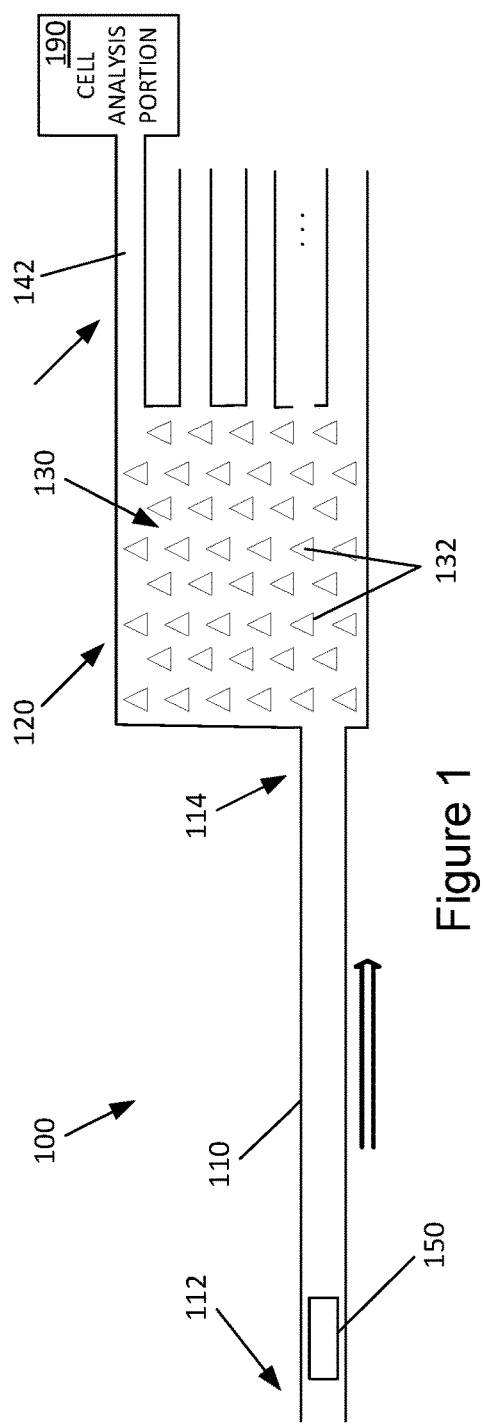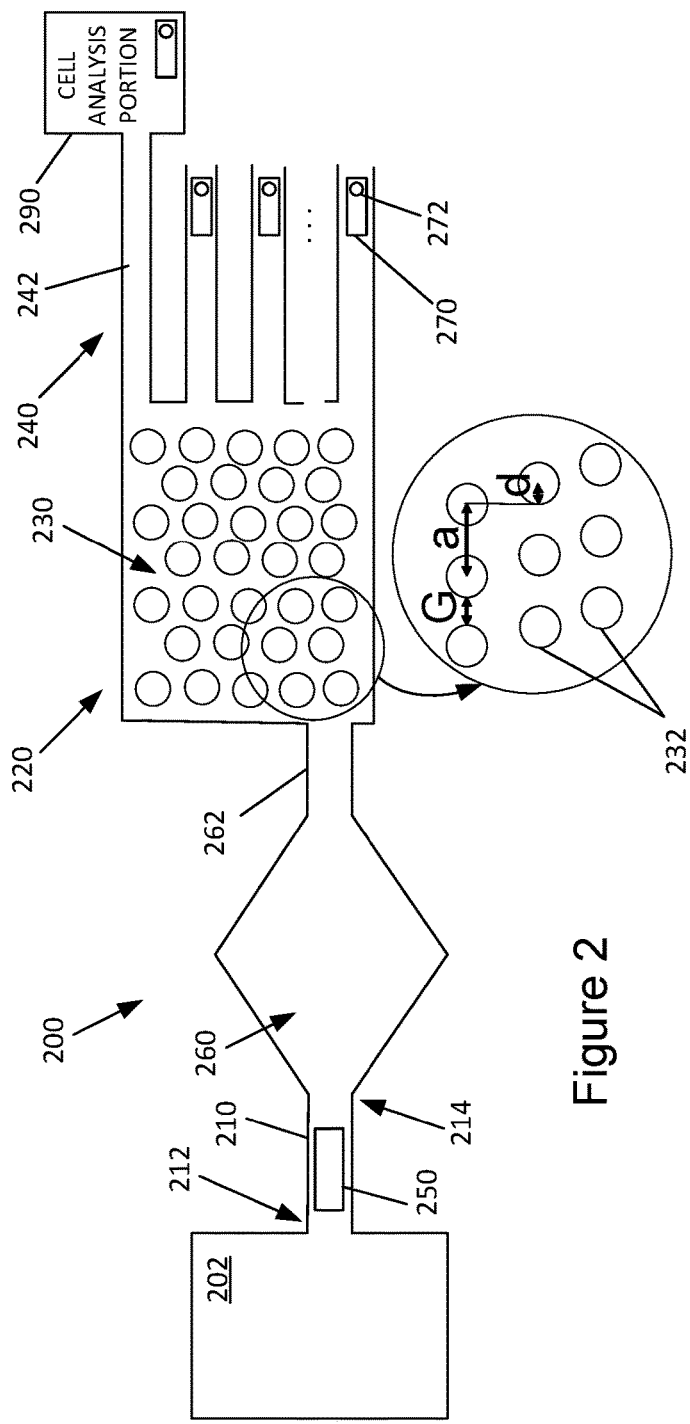
Figure 1
Figure 2

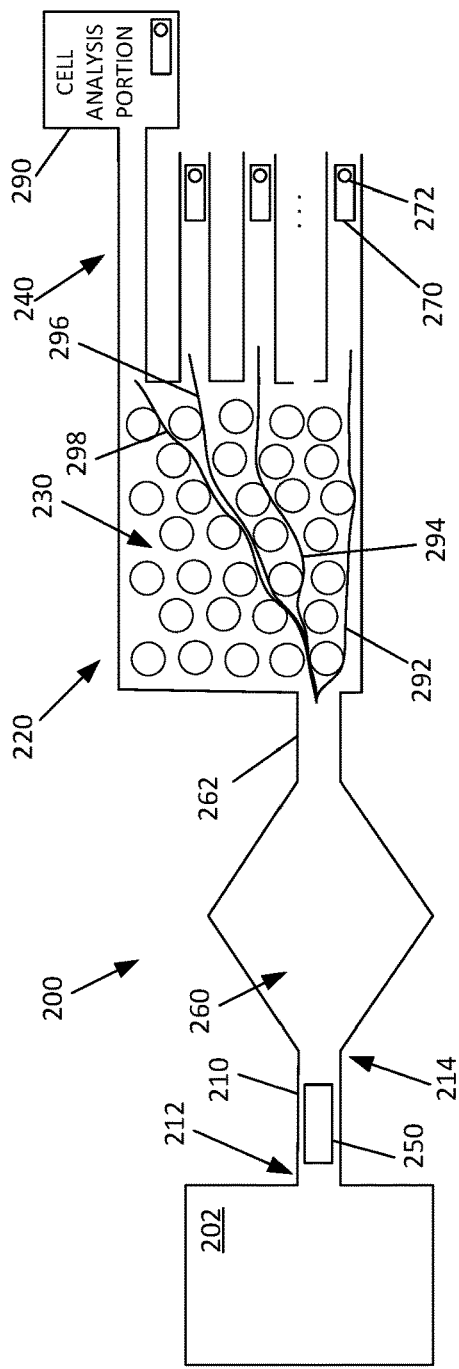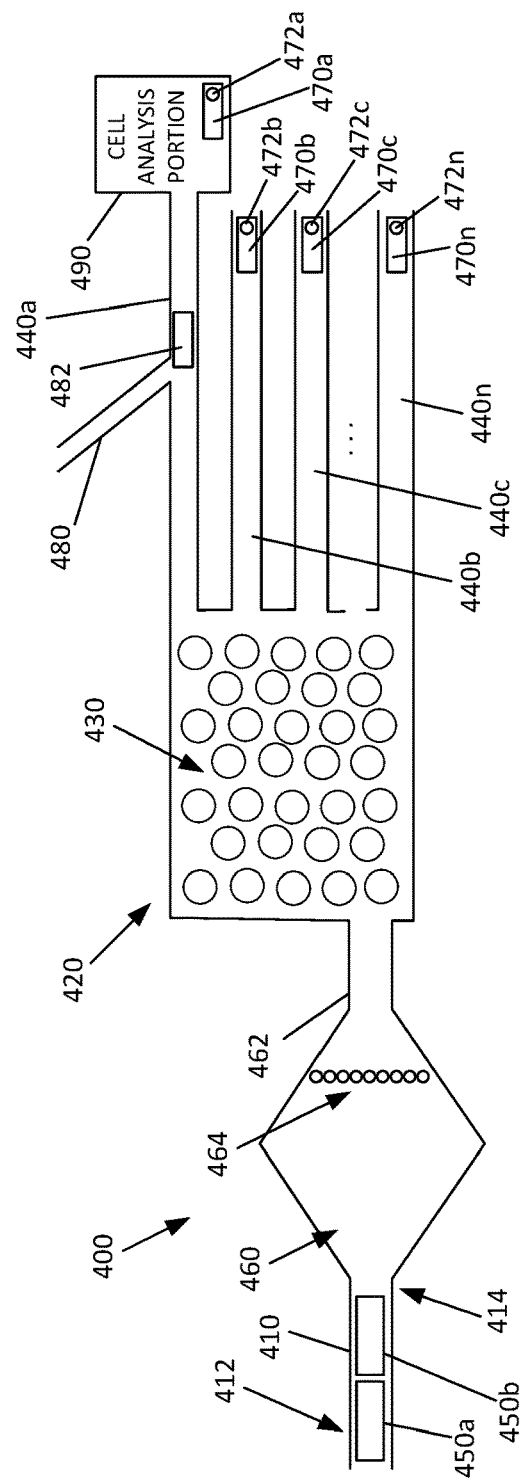
Figure 3
Figure 4

PARTICLE SEPARATION AND ANALYSIS

BACKGROUND

Microfluidic devices are increasingly commonplace in a variety of environments. For example, microfluidic devices have applicability in biology, medicine, genetics and numerous other fields. Microfluidic devices may include such devices as lab-on-a-chip micro-total analytical systems and can carry, analyze, or process various particles, DNA, proteins, biomarkers, sugars (glucose), large and small bio-organic and inorganic molecules, bacteria, biological cells, viruses and other solid and soft objects of microscale. Various microfluidic devices may include fluids flowing through narrow channels. In a lab-on-a-chip, for example, blood cells may be moved from one chamber to another, such as from an input port to a reaction chamber. In other examples, the microfluidic device may be provided for the flow of other fluids or materials, such as blood or other biological fluids.

BRIEF DESCRIPTION OF THE DRAWINGS

For a more complete understanding of various examples, reference is now made to the following description taken in connection with the accompanying drawings in which:

FIG. 1 illustrates an example system for separation and analysis of cells;

FIG. 2 illustrates another example system for separation and analysis of cells;

FIG. 3 illustrates separation and analysis of cells in the example system of FIG. 2;

FIG. 4 illustrates another example system for separation and analysis of cells;

DETAILED DESCRIPTION

Figure 5:
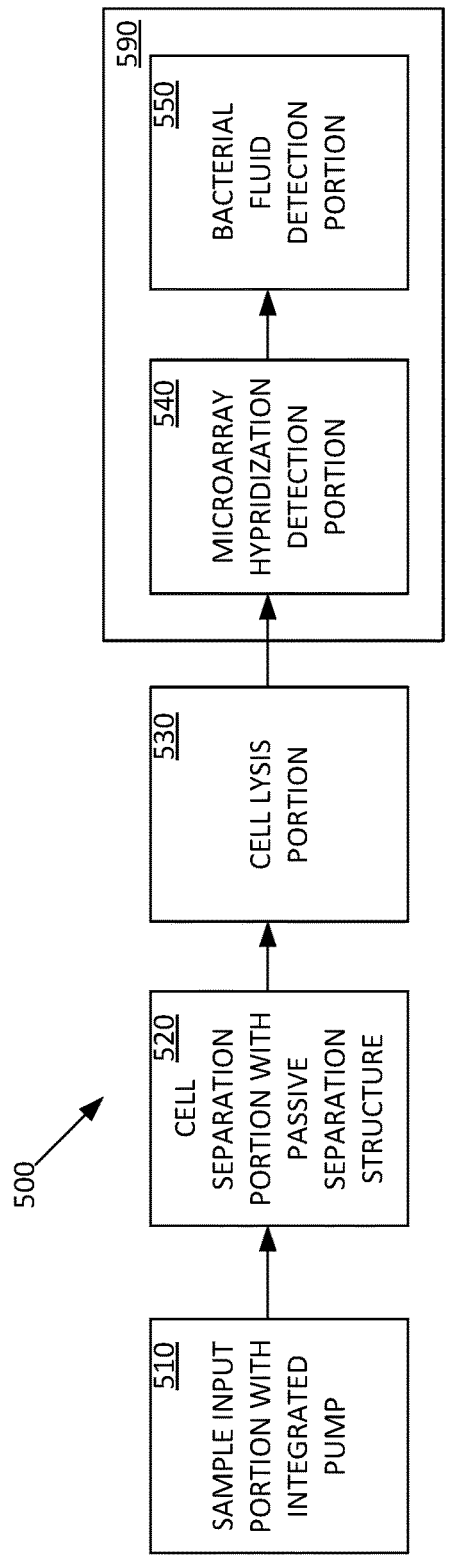
FIG. 5 is a schematic illustration of another example system for separation and analysis of cells.

As noted above, microfluidic devices may be provided to flow fluids through narrow channels to, for example, reaction chambers. In various examples, the fluids may include any number of particles within a flow. A reaction chamber or another output of the channels may use the particles in a separated or concentrated condition. Accordingly, the various particles in a flow are separated (e.g., sorted or categorized) for use within the microfluidic device or for output from the microfluidic device. In other examples, the various particles may be purified, or concentrated.

In order to separate the particles, some devices use a system of sensors and valves to open a corresponding channel to direct a particle into an appropriate channel. Such sensors and valves typically result in slowing of the flow upstream of the valve. Further, such sensors and valves have the potential to fail, resulting in failure of sorting in all output channels.

Further, categorizing or flow of particles may be facilitated with the use of external pumps. External pumps (e.g., syringe pumps or capillary pumps) may increase complexity and expense by requiring a pump to be outside the lab-on-a-chip, for example.

Analysis of separated particles, such as cells, is generally performed in separate systems, or kits, from the system used for separation, or concentration. This results in complexity and possibility of failure during, for example, transition from one system to another.

Various examples described herein relate to separation or concentration of particles in, for example, a microfluidic device. A flow of particles containing at least two categories of particles is sorted by directing each particle from an input channel through a chamber of passive separation structures. The passive separation structure may include columns, or posts, that are spaced apart in a manner which directs particles in the flow along different paths based on the size of the particles. The device includes at least one integrated pump, such as an inertial pump, in the input channel or an output channel to facilitate flow of the particles. In various examples, the integrated pumps are thermal inkjet resistors. In other examples, inertial pumps may be actuated by a piezo-drive membrane or by any other displacement device driven force such as, for example, electrostatic, pneumatic, magneto-strictive, magnetic or similar forces. In some examples, the integrated pump in at least one output channel is operable to direct the separated particles to a drop-on-demand outlet. Various examples include post-processing of the separate particles, including identification of cells in an output channel. In this regard, the output channel may include regions comprising arrays of antibodies. The particle (e.g., cell) in an output channel may be identified based on the region in which the particle binds to an antibody. Thus, an integrated system may be provided which includes pumping, separation and analysis of various particles.

Referring now to the Figures, FIG. 1 illustrates an example system for separation and analysis of cells. The example system may be any of a variety of devices, such as microfluidic devices, lab-on-a-chip, or micro total analytical systems, for example. In the example of FIG. 1, the example system 100 includes an input channel 110 with a first end 112 and a second end 114. The input channel 110 may receive particles therein through the first end 112. An arrow in the input channel 110 illustrated in FIG. 1 indicates the direction of flow of the particles. As used herein, a particle may include, but not limited to, a solid substance, bio-cells, bacteria, viruses, protein globules, biological eukareotic cells, prokareotic cells, cell components. In some examples, the particles may include any of a variety of particles such as, but not limited to, blood cells or other cells, beads, solids, etc. In some examples, particles may be microscopic objects ranging in size between about 1 nanometer and about 1 millimeter. In various examples, the input channel 110 may be a long and/or narrow channel.

In various examples, the example system 100 is a microfluidic device, and the input channel 110 is a microfluidic channel. In one example, the input channel 110 has a cross-sectional width of between about 10 μm and about 500 μm. Various examples of the system 100 may be formed by performing various microfabrication and/or micromachining processes on a substrate to form and/or connect structures and/or components. The substrate may comprise a silicon based wafer or other such similar materials used for microfabricated devices (e.g., glass, gallium arsenide, plastics, etc.). Examples may comprise microfluidic channels, fluid actuators, and/or volumetric chambers. Microfluidic channels and/or chambers may be formed by performing etching, microfabrication processes (e.g., photolithography), or micromachining processes in a substrate. Accordingly, microfluidic channels and/or chambers may be defined by surfaces fabricated in the substrate of a microfluidic device. In some implementations, microfluidic channels and/or chambers may be formed by an overall package, wherein multiple connected package components that combine to form or define the microfluidic channel and/or chamber.

In various examples, a stream of particles flowing through the input channel 110 may include two, three, or more different categories of particles. In various examples, the categories of particles may include, but not limited to, solid particles, soft particles, gas bubbles, biological cells, bacteria, droplets of fluid (e.g., immiscible fluid, also referred to as colloidal particles), and clusters thereof. A category may include a particular type of particle or a group of types of particles. For example, in one example, a category may include all blood cells, and in another example, a category may include a particular type of blood cell. In one example, the sensor is positioned to allow detection of a particle and identification of at least one parameter associated with the particle which allows categorization of the particle.

In the example of FIG. 1, the example system 100 includes a separation chamber 120. The separation chamber 120 is in fluid communication with the second end 114 of the input channel 110. Thus, the separation chamber 120 may receive a flow of particles flowing through the input channel 110. In various examples, the separation chamber 120 includes a passive separation structure 130 to separate particles in a flow based on the size of the particles. The passive separation structure 130 of the example system 100 includes an array of columns 132, or posts, that are arranged to facilitate separation of particles in the flow based on the size of the particles. For example, the columns 132 may be arranged in accordance with principles of deterministic lateral displacement (DLD), which is described below in greater detail with reference to FIG. 2.

In the illustration of FIG. 1, the flow of particles enters the separation chamber 220 from the left side. As the particles flow through the separation chamber 220, the array of columns 132 causes the particles to separate according to size. In this regard, the example system 100 includes at least two output channels 140. Each output channel is in fluid communication with the separation chamber 120 and positioned to receive separated particles. Thus, each output channel 140 is positioned to receive particles of a certain size or range of sizes.

In various examples, the passive separation structure 130 separates the particles in the flow into at least two flow paths based on a size of the particles. As noted above, each output channel 140 is positioned to receive particles of a certain size or range of sizes. In this regard, each flow path is directed to one of the output channels 140. In the example system 100 of FIG. 1, a selected output channel 142 of the output channels 140 is positioned to receive cell-sized particles. Thus, a specific flow path is associated with particles sizes that correspond to a cell.

The example system 100 of FIG. 1 is provided with an integrated pump 150 to facilitate flow of particles through the separation chamber 120. While the example system 100 of FIG. 1 is provided with the integrated pump 150 in the input channel 110, in various examples, the integrated pump 150 may be positioned within the input channel, an output channel 140 or a combination thereof. Thus, the integrated pump 150 may be a push pump provided in the input channel 110, as shown in FIG. 1, or a pull pump provided in an output channel 140.

In the example in which the example system 100 is a microfluidic device, each integrated pump 150 may be an inertial pump. As used herein, an inertial pump corresponds to a fluid actuator and related components disposed in an asymmetric position in a microfluidic channel, where an asymmetric position of the fluid actuator corresponds to the fluid actuator being positioned less distance from a first end of a microfluidic channel as compared to a distance to a second end of the microfluidic channel. Accordingly, in some examples, a fluid actuator of an inertial pump is not positioned at a mid-point of a microfluidic channel. The asymmetric positioning of the fluid actuator in the microfluidic channel facilitates an asymmetric response in fluid proximate the fluid actuator that results in fluid displacement when the fluid actuator is actuated. Repeated actuation of the fluid actuator causes a pulse-like flow of fluid through the microfluidic channel.

In some examples, an inertial pump includes a thermal actuator having a heating element (e.g., a thermal resistor) that may be heated to cause a bubble to form in a fluid proximate the heating element. In such examples, a surface of a heating element (having a surface area) may be proximate to a surface of a microfluidic channel in which the heating element is disposed such that fluid in the microfluidic channel may thermally interact with the heating element. In some examples, the heating element may comprise a thermal resistor with at least one passivation layer disposed on a heating surface such that fluid to be heated may contact a topmost surface of the at least one passivation layer. Formation and subsequent collapse of such bubble may generate unidirectional flow of the fluid. As will be appreciated, asymmetries of the expansion-collapse cycle for a bubble may generate such flow for fluid pumping, where such pumping may be referred to as "inertial pumping." In other examples, a fluid actuator corresponding to an inertial pump may comprise a membrane (such as a piezoelectric membrane) that may generate compressive and tensile fluid displacements to thereby cause fluid flow.

The example system 100 of FIG. 1 further includes a cell analysis portion 190. The cell analysis portion 190 is coupled to the selected output channel 142 described above. In the example system 100 of FIG. 1, a single output channel 142 is coupled to a cell analysis portion 190. The cell analysis portion 190 may be provided to perform an analysis associated with the cells in the selected output channel 142. In other examples, additional channels may be provided with corresponding cell analysis portions. Further, in other examples, a single cell analysis portion may be coupled to multiple output channels 140. In this regard, the cell analysis portion 190 may perform analysis on a variety of sizes of cells.

Referring now to FIG. 2, another example system for example system for separation and analysis of cells is illustrated. The example system 200 of FIG. 2 is similar to the example system 100 of FIG. 1 and includes an input channel 210, a separation chamber 220, a set of output channels 240, and a cell analysis portion 290. Similar to the example system 100 of FIG. 1, the input channel 210 has a first end 212 and a second end 214. The separation chamber 220 is in fluid communication with the second end 214 of the input channel 210. The separation chamber 220 includes a passive separation structure 230 which includes an array of columns 232 arranged to facilitate separation of particles in the flow based on the size of the particles. The flow of particles is separated into different flow paths based on the size of the particles in the flow, with at least one of the flow paths corresponding to cell-sized particles. The cell analysis portion 290 is coupled to a selected output channel 242 which is associated with a flow path corresponding to cell-sized particles. Thus, the cell analysis portion may receive cells (or cell-sized particles) for analysis thereof.

The example system 200 of FIG. 2 is provided with an integrated pump 250 in the input channel 210. In order to reduce pulsing in the separation chamber 220 due to operation of the integrated pump 250, the example system 200 is provided with a dampening chamber 260 positioned between the second end 214 of the input channel 210 and the separation chamber 220. The dampening chamber 260 is in fluid communication with the separation chamber 220 through a focusing channel 262. The dampening chamber 260 allows for a more steady flow of particles into the separation chamber 220. In the example system 200 of FIG. 2, a sample reservoir 202 is provided for supplying a flow of particles to the input channel 210. In various examples, the integrated pump 250 may draw particles from the sample reservoir 202 for flow through the input channel 210, the dampening chamber 260 and the separation chamber 220. In various examples, the sample reservoir 202 may be replaceable or refillable.

In addition to the integrated pump 250 in the input channel, each output channel 240 of the example system 200 is provided with an integrated pump 270. The integrated pumps 270 in the output channels 240 are coupled to nozzles 272 to allow ejection of the separated particles, for example. The nozzles 272 may allow the separated particles to be selectively drawn or dropped as desired. In the case of the selected output channel 242, the integrated pump may be provided in the selected output channel 242 or, as illustrated in the example of FIG. 2, within the cell analysis portion 290. In one example, the integrated pumps 270 in the output channels 240 include a piezo element, forming a piezoelectric micro pump. In various examples, the piezo element and the nozzle 272 form a drop ejector to allow the separated particles to be drawn or dropped from the output channel 240.

As noted above, the passive separation structure 230 includes an array of columns 232 that may be arranged in accordance with DLD principles. DLD uses a specific arrangement of obstacles, such as columns 232, to control the path, or trajectory, of particles to separate particles larger than a critical diameter from those smaller than the critical diameter through collisions with the obstacles. In a flow, when a particle is larger than the critical diameter, its center is positioned such that collision with an obstacle causes the larger particle to flow to one side of the obstacle. Meanwhile, collision of objects smaller than the critical diameter the same obstacle causes the smaller particle to flow to the other side of the obstacle.

In various examples, the columns 232 may be formed with any of a variety of shapes, or cross-sectional shape. For example, the columns 232 may be formed as circular, triangular or any polygonal shape, for example. Further, the array of columns 232 may be formed with the columns 232 have a particular size (e.g., cross-sectional diameter), a column spacing (G) and a column pitch (d/a). The array of columns may be formed to separate particles based on a critical diameter, which may be calculated as $2*\alpha*G*pitch$, where a is a non-dimensional correction factor determined as $sqrt(a/3d)$. In one example, the array of columns 232 is formed to separate particles of 0.75 µm. In this example, the columns 232 may be formed as circular cylinders having a cross-sectional diameter of 5 µm, a pillar spacing (G) of 5 µm and a pitch (d/a) of 0.01. In this arrangement, particles larger than 0.75 µm are separated from particles smaller than 0.75 µm.

In various examples, the separation chamber 220 may be divided into zones to further separate particles. For example, in a first zone, the particles may be divided based on a critical diameter of 0.75 µm, as described above. In a downstream zone, the particles larger than 0.75 µm may be further separated with a critical diameter of 1.00 µm. Thus, three paths may be formed with a first path for particles smaller than 0.75 µm, a second path for particles larger than 0.75 µm but smaller than 1.00 µm, and a third path for particles larger than 1.00 µm. Of course, the particles may be separated into as many size categories as desired or as may be accommodated by the size of the separation chamber.

In this regard, FIG. 3 illustrates separation of particles in the example system 200 of FIG. 2. FIG. 3 illustrates separation of flow into four paths. As noted above, any practical number of paths may be formed in the separation chamber 220. In the example of FIG. 3, the passive separation structure 230 results in particles in four size categories being directed along a corresponding path 292, 294, 296, 298. Each of the paths 292, 294, 296, 298 corresponds to one of the output channels 240.

In various examples described and illustrated herein, an inlet of the flow of particles into the separation chamber 220 is positioned to provide a flow to a particular region of the separation chamber 220. For example, FIGS. 2 and 3 illustrate the focusing channel 262 being in fluid communication with a lower left portion of the separation chamber 220. It will be understood that, in various examples, an input to the separation chamber, such as the focusing channel 262 or the input channel 110 of FIG. 1, may be positioned to interface with other regions of the separation chamber 220. For example, the focusing channel 262 may be coupled to a central or upper left portion of the separation chamber 220. In this regard, the passive separation structure 230 may form paths 292, 294, 298, 298 from the specific input region to the various output channels 240.

Referring now to FIG. 4, another example system 400 for example system for separation and analysis of cells is illustrated. The example system 400 of FIG. 4 is similar to the example system 200 of FIG. 2. In this regard, the example system 400 includes an input channel 410 with a first end 412 and a second end 414, a separation chamber 420 with a passive separation structure 430 formed with an array of columns 432, a set of output channels 440, and a cell analysis portion 490. The cell analysis portion 490 is coupled to a selected output channel 442 which is associated with a flow path corresponding to cell-sized particles. Thus, the cell analysis portion may receive cells (or cell-sized particles) for analysis thereof.

The example system 400 further includes a dampening chamber 460 in fluid communication with the separation chamber 420 through a focusing channel 462. The example system 400 of FIG. 4 is provided with integrated pumps 450a, 450b in the input channel 410, as well as integrated pumps 470a-n in the output channels 440a-n. As noted above, each integrated pump 470a-n in the output channels 440a-n is coupled to a nozzle 472a-n.

The example system 400 of FIG. 4 is further provided with a reagent input channel 480. The reagent input channel 480 is in fluid communication with a first output channel 440a. The reagent input channel 480 may be used to mix a reagent, such as a lysing agent, with the flow of separated particles (e.g., concentrated or purified) in the corresponding output channel 440a. In this regard, a mixing pump 482 may be provided to facilitate or control the mixing of the separate particles with a reagent in the first output channel 440a. The mixing pump 482 may be similar to the pumps 450a,b and 470a-n and may be an integrated pump (e.g., an inertial pump). As described in various examples below, the reagent may be used to prepare the separated particles in the selected output channel 440 for analysis in the cell analysis portion 490.

In the example system 400 of FIG. 4, the dampening chamber 460 is provided with dampening features 464 to facilitate reduction of pulsing in the separation chamber 420. In various example, the features may include an array of orifices, an elastic membrane or other such features. In one example, the dampening features 464 are orifices that are round, rectangular or other geometric shape.

Referring now to FIG. 5, another example system for separation and analysis of cells is schematically illustrated. The example system 500 of FIG. 5 may be implemented as a microfluidic device, for example, for analysis of various samples. In this regard, the example system 500 includes a sample input portion 510. In various examples, the sample input portion 510 includes an input channel, such as the input channel 110, 210 or 410 described above with references to FIGS. 1-4. In some examples, the sample input portion 510 further includes a sample reservoir, such as the sample reservoir 202 of the example system 200 illustrated in FIGS. 2 and 3. Further, some examples of the sample input portion 510 includes a dampening portion such as the dampening portion 260, 460 of the example systems 200, 400 described above with reference to FIGS. 2-4. In various examples, the sample input portion 510 is provided with an integrated pump, such as an inertial pump.

The example system 500 of FIG. 5 further includes a cell separation portion 520. The cell separation portion 520 includes a separation chamber, such as the separation chamber 120, 220, 420 described above with reference to FIG. 1-4. In this regard, the cell separation portion 520 includes a passive separation structure formed with an array of columns to separate particles into at least two paths, at least one of which is associated with cell-sized particles. The cell separation portion 520 of the example system 500 includes output channels, and a selected one of the output channels is positioned to receive the cell-sized particles.

The example system 500 includes a cell lysis portion 530 for lysing of cells that are received in the selected output channel described above. As used herein, lysing may include breaking down of the membrane of the cell to, for example, release contents therein. For example, genetic material, such as DNA fragments, may be released when a cell is lysed.

In the example system 500 of FIG. 5, the cell lysis portion 530 may include a reagent input channel, such as the reagent input channel 480 described above with reference to FIG. 4. The reagent input channel is coupled to the selected output channel with the cell-sized particles and may be used to introduce a lysing agent into the flow in the selected output channel. As noted above, a pump may be provided to facilitate mixing of the lysing agent with the cell-sized particles in the selected output channel.

The example system 500 of FIG. 5 is provided with a cell analysis portion 590. In the example system 500, the cell analysis portion 590 is coupled to the cell lysis portion 530 to receive, for example, biological material from the lysed cells. The cell analysis portion 590 includes at least one detection portion to, for example, identify characteristics of the biological material. In the example illustrated in FIG. 5, the cell analysis portion includes a microarray hybridization detection portion 540 and a bacterial fluid detection portion 550. Other examples may include only one of the two detection portions 540, 550.

The microarray hybridization detection portion 540 is provided to detect characteristics of biological material such as electrochemical properties or fluorescence. In various examples, the microarray hybridization detection portion 540 includes a microchip with microscopic DNA spots (e.g., immobilized nucleic acid polymer chains). Various spots may be provided with probes (e.g., specific DNA sequences) to detect corresponding biological material through hybridization of the probe and the corresponding biological material. The hybridization may be detected via, for example, fluorescence or chemiluminescence. In some examples, other methods of detection may be used, such as enzyme amplification. For example, an enzyme attached to the probes works on a substrate. When the substrate interacts with the enzyme, a fluorescent electrochemically active material, or a product that has a high visible light absorption coefficient, is produced. One example of such an enzyme is horseradish peroxidase.

The bacterial fluid detection portion 550 may be provided to detect biological material that may be provided in a fluid, such as blood, urine or spinal fluid, for example. In various examples, the bacterial fluid detection portion 550 may be used in place of or in addition to the microarray hybridization detection portion 540. For example, the bacterial fluid detection portion may receive biological material directly from the cell lysing portion 530 or from the cell separation portion 520. In various examples, the biological material may include *Salmonella Campylobacter, E. Coli, Listeria, Clostridium perfringens*, or other bacteria.

Thus, the example systems described above, such as the example system 500 of FIG. 5, provide an integrated system which includes pumping, separation and analysis of various particles, such as cells. The integrated system results in a user-friendly system with minimizing of external components, such as external pumps. Further, the integrated system reduces or eliminates handling or transferring of, for example, separated or concentrated particles (e.g., cells).

Figure 6:
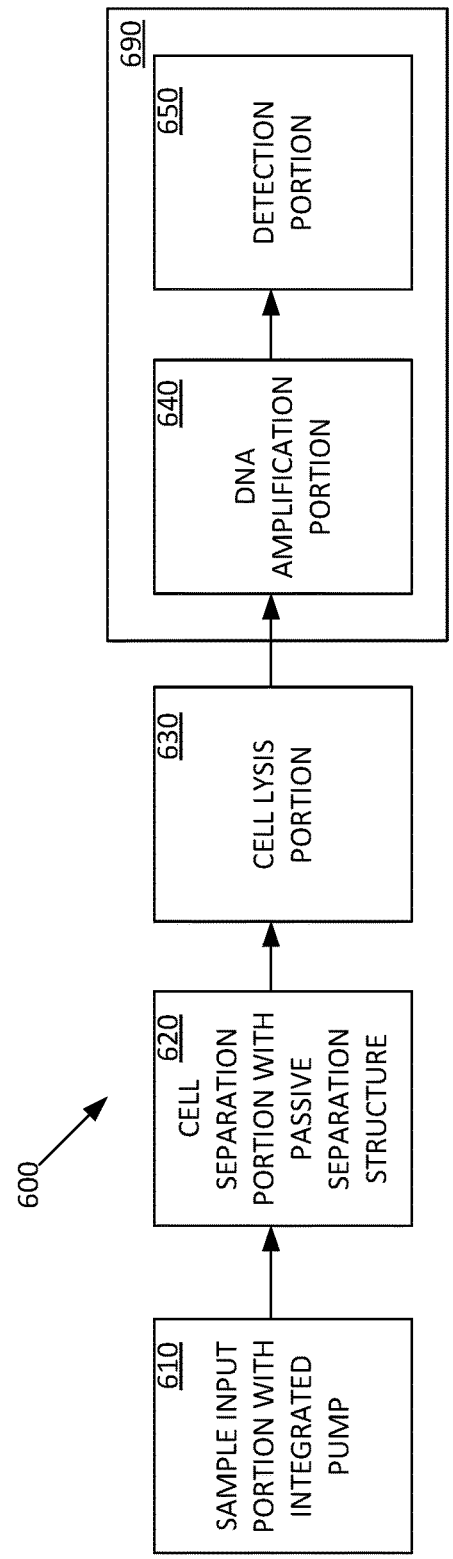
FIG. 6 is a schematic illustration of another example system for separation and analysis of cells.

Referring now to FIG. 6, a schematic illustration of another example system 600 for separation and analysis of cells is provided. The example system 600 of FIG. 6 is similar to the example system 500 described above with reference to FIG. 5. In this regard, the example system 600 includes a sample input portion 610, a cell separation portion 620, a cell lysis portion 630, and a cell analysis portion 690. In the example system 600 of FIG. 6, the cell analysis portion 690 includes a DNA amplification portion 640 positioned between the cell lysis portion 630 and a detection portion 650. The detection portion 650 may be similar to the various detection portions described above, such as the microarray hybridization detection portion 540 or the bacterial fluid detection portion 550, for example.

The DNA amplification portion 640 is provided to amplify biological material from the lysed cells. In this regard, DNA amplification portion 640 is positioned to receive biological material from the cell lysis portion 630 and to provide the amplified biological material to the detection portion 640. The DNA amplification portion 640 allows for amplification of the sample size of concentrated, separated and/or lysed biological material received by the cell analysis portion 690. Thus, a small volume of the sensor may be used for analysis/detection, resulting in smaller volumes of the sample, reagent or other components. Further, the smaller sample size may result in shorter time for separation or concentration of cells, for example.

Figure 7:
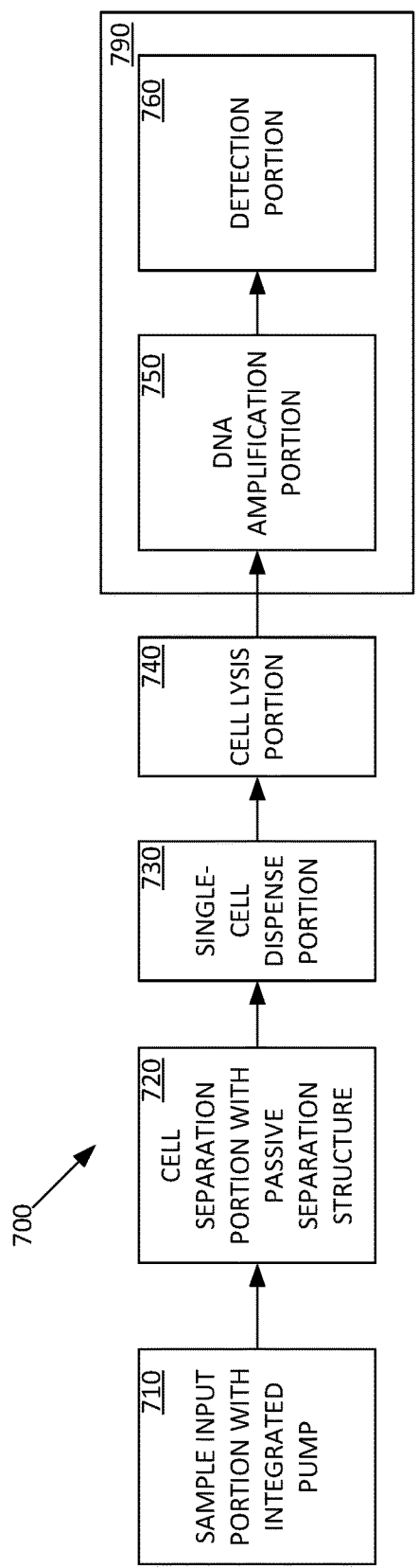
FIG. 7 is a schematic illustration of another example system for separation and analysis of cells.

Referring now to FIG. 7, a schematic illustration of another example system 700 for separation and analysis of cells is provided. The example system 700 of FIG. 7 is similar to the example system 600 described above with reference to FIG. 6. In this regard, the example system 700 includes a sample input portion 710, a cell separation portion 720, a cell lysis portion 740, and a cell analysis portion 790. In the example system 700 of FIG. 7, the cell analysis portion 790 includes a DNA amplification portion 750 positioned between the cell lysis portion 740 and a detection portion 760. The example system 700 of FIG. 7 further includes a single-cell dispense portion 730. The single-cell dispense portion 730 is provided to allow single cells, or small controlled amount of cells, to be processed from the cell separation portion 720. Thus, single cells may be lysed by the cell lysis portion 740 and analyzed by the cell analysis portion 790. In this regard, single-cell information may be obtained, and cell-level statistics may be calculated.

Figure 8:
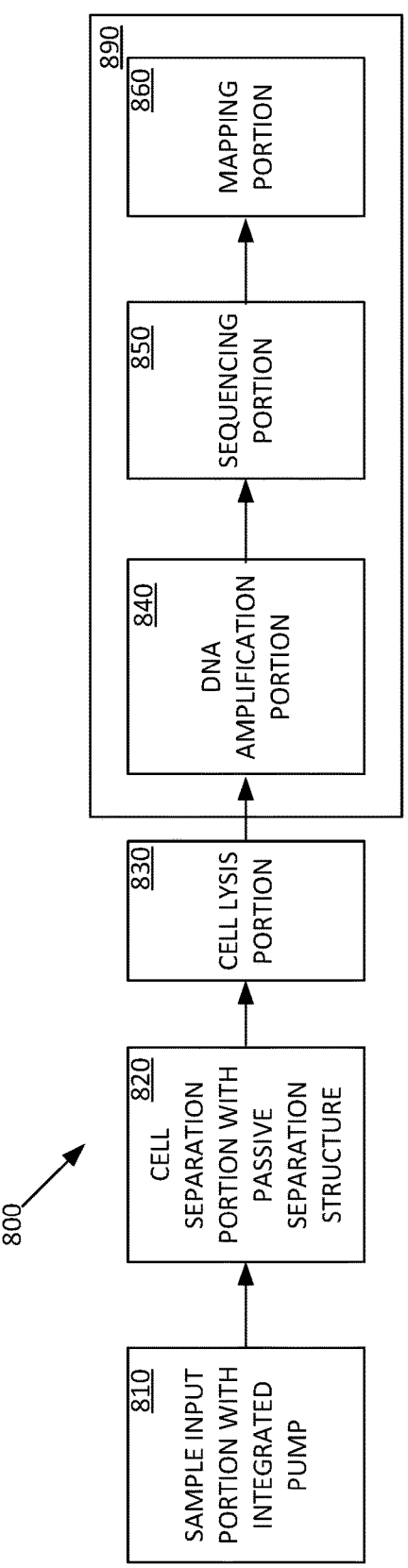
FIG. 8 is a schematic illustration of another example system for separation and analysis of cells.

Referring now to FIG. 8, a schematic illustration of another example system 800 for separation and analysis of cells is provided. The example system 800 of FIG. 8 is similar to the example system 600 described above with reference to FIG. 6. In this regard, the example system 800 includes a sample input portion 810, a cell separation portion 820, a cell lysis portion 830, and a cell analysis portion 890. In the example system 800 of FIG. 8, the cell analysis portion 890 includes a DNA amplification portion 840 positioned to receive biological material from the cell lysis portion 830. Thus, the DNA amplification portion 840 may be provided to amplify biological material (e.g., DNA fragments) from the lysed cells. The cell analysis portion 890 further includes a sequencing portion 850 to obtain a genetic sequence from the amplified biological material. In various examples, the sequencing portion 850 may be provided to identify a DNA fragment and obtain genetic sequence information from the DNA fragment. The genetic sequence information obtained by the sequencing portion 850 may be used to identify a condition using a mapping portion 860. In this regard, the mapping portion 860 may utilize machine learning to progressively improve its ability to match patterns in the genetic sequences that may be associated with a variety of conditions, such as cancers, diabetes or any of a variety of other conditions.

Figure 9:
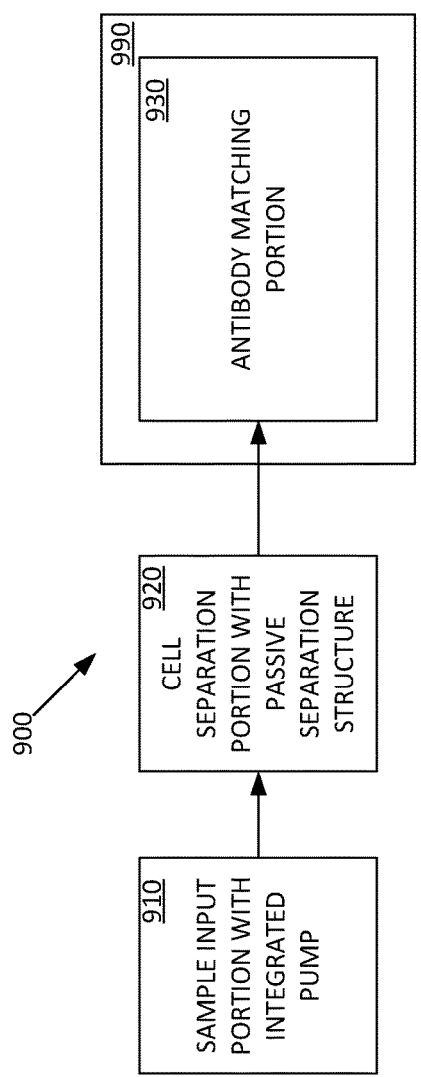
FIG. 9 is a schematic illustration of another example system for separation and analysis of cells.

Referring now to FIG. 9, a schematic illustration of another example system 900 for separation and analysis of cells is illustrated. The example system 900 of FIG. 9 includes a sample input portion 910 similar to the sample input portions 510, 610, 710, 810 described above. In this regard, the sample input portion 910 includes an input channel and, in some examples, further includes a sample reservoir and/or a dampening portion. In various examples, the sample input portion 910 is provided with an integrated pump, such as an inertial pump.

The example system 900 of FIG. 9 further includes a cell separation portion 920. As described above, the cell separation portion 920 includes a separation chamber, such as the separation chamber 120, 220, 420 described above with reference to FIG. 1-4 with a passive separation structure formed with an array of columns to separate particles into at least two paths, at least one of which is associated with cell-sized particles. The cell separation portion 920 of the example system 900 includes output channels, and a selected one of the output channels is positioned to receive the cell-sized particles.

The example system 900 of FIG. 9 is provided with a cell analysis portion 990. In the example system 900, the cell analysis portion 990 is coupled to the selected output channel to receive cell-sized particles. The cell analysis portion 990 includes an antibody matching portion 930. In various examples, the antibody matching portion 930 including an array of cell identification regions. Each cell identification region includes antibodies to bind to a corresponding cell. In this regard, the cell analysis portion 990 may include various other components, such as detection portions to identify regions in which binding has occurred between cells and corresponding antibodies.

Figure 10:
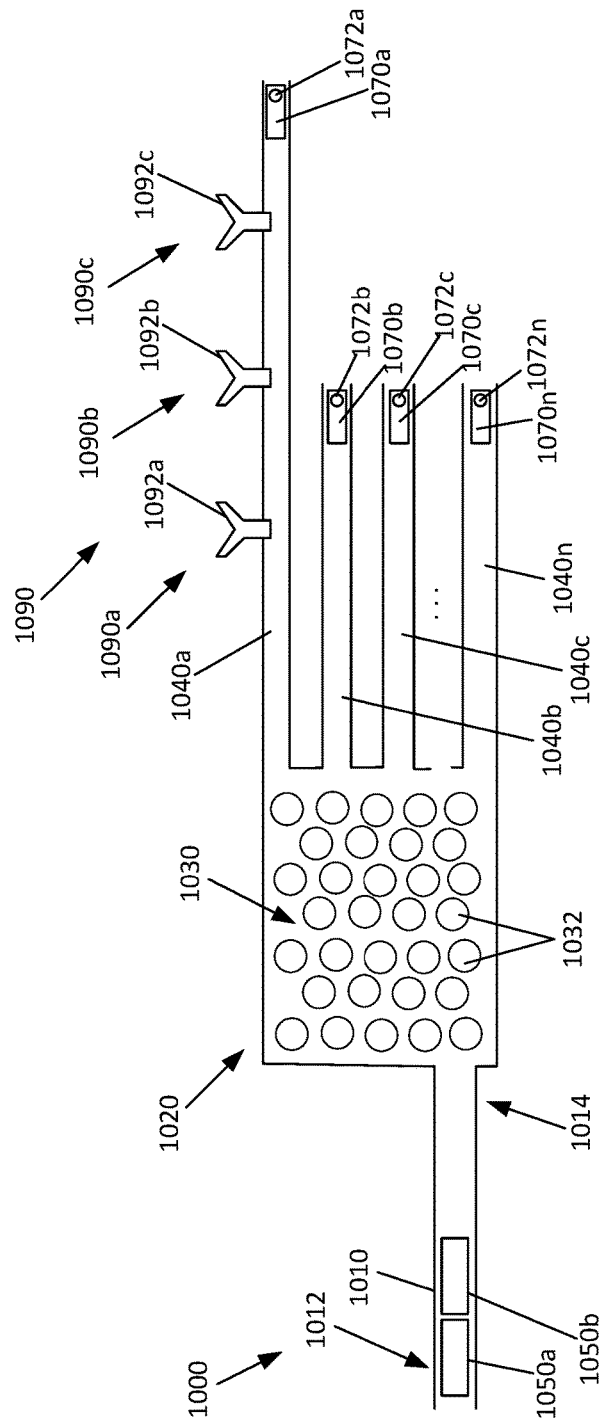
FIG. 10 illustrates another example system for separation and analysis of cells.

Referring now to FIG. 10, another example system 1000 for separation and analysis of cells is illustrated. The example system 1000 is similar to the example system 200 of FIG. 2 and includes an input channel 1010 with a first end 1012 and a second end 1014, integrated pumps 1050a, 1050b, a separation chamber 1020 with a passive separation structure 1030 formed with an array of columns 1032, a set of output channels 1040a-n and a cell analysis portion 1090. The cell analysis portion 1090 is coupled to a selected output channel 1040a which is associated with a flow path corresponding to cell-sized particles. Thus, the cell analysis portion 1090 may receive cells (or cell-sized particles) for analysis thereof.

The cell analysis portion 1090 of the example system 1000 of FIG. 10 is provided with an array of cell identification regions 1090a-c. Each cell identification region 1090a-c is provided with antibodies 1092a-c that may be embedded in the corresponding region 1090a-c. In one example, the antibodies 1092a-c may be embedded on a microchip positioned in the cell analysis portion 1090. The antibodies 1092a-c in each cell identification region 1090a-c may be selected to bind to a specific corresponding cell, such as the cell 1094 shown as binding to the antibody 1092c in the cell identification region 1090c. A detection portion (not shown in FIG. 10) may be provided to determine the cell identification regions 1090a-c with binding cells to facilitate identification of cells in the input sample.

In the example system 1000 of FIG. 10, each output channel 1040a-n includes an integrated pump 1070a-n and a corresponding nozzle 1072a-n to facilitate flow of particles through the output channels 1040a-n. The pump 1070a and nozzle 1072a corresponding to the selected output channel 1040a with the cell analysis portion 1090 are provided within or downstream of the cell identification regions 1090a-c.

Figure 11:
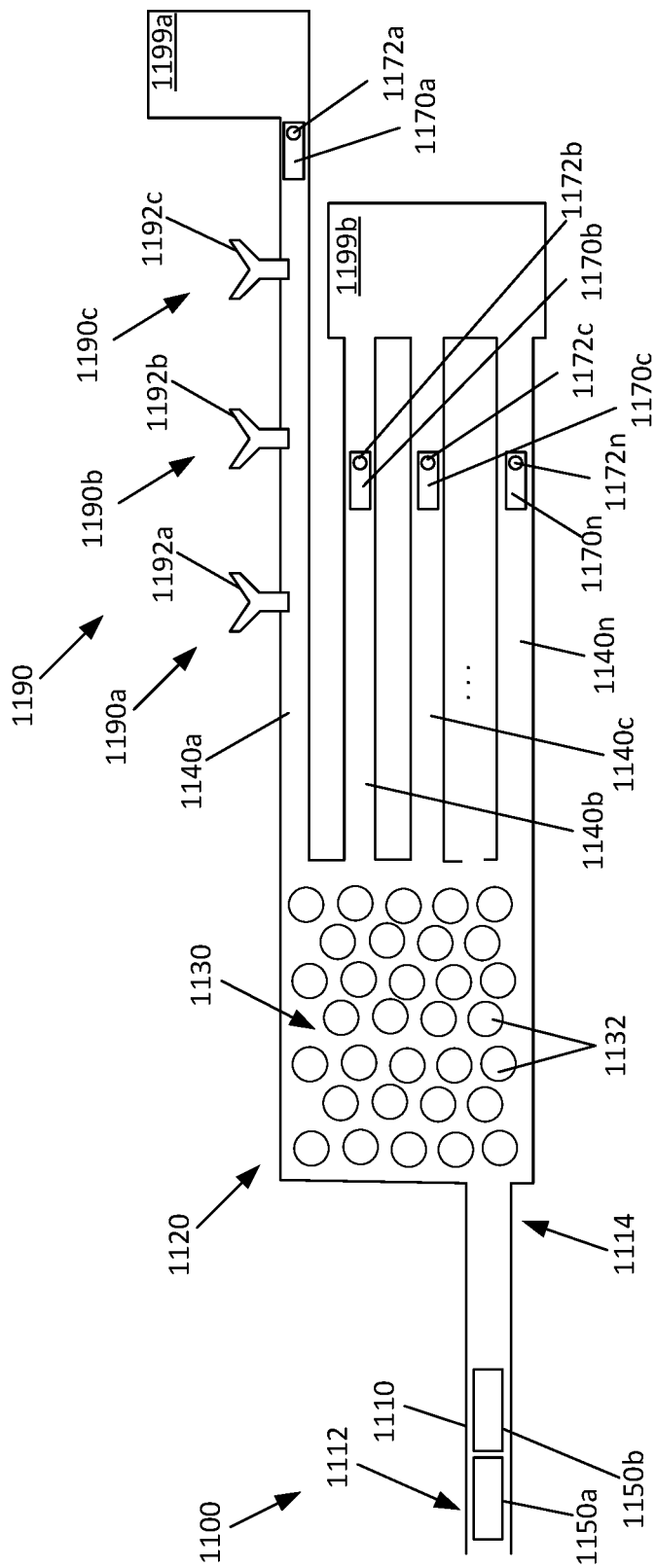
FIG. 11 illustrates another example system for separation and analysis of cells.

Referring now to FIG. 11, another example system 1100 for separation and analysis of cells is illustrated. The example system 1100 is similar to the example system 1000 described above with reference to FIG. 10. In this regard, the example system 1100 of FIG. 11 includes an input channel 1110 with a first end 1112 and a second end 1114, integrated pumps 1150a, 1150b, a separation chamber 1120 with a passive separation structure 1130 formed with an array of columns 1132, a set of output channels 1140a-n and a cell analysis portion 1190. The cell analysis portion 1190 is coupled to a selected output channel 1140a which is associated with a flow path corresponding to cell-sized particles. Thus, the cell analysis portion 1190 may receive cells (or cell-sized particles) for analysis thereof.

Similar to the example system 1000 of FIG. 10, the cell analysis portion 1190 of the example system 1100 of FIG. 11 is provided with an array of cell identification regions 1190a-c, each cell identification region 1090a-c being provided with antibodies 1192a-c selected to bind to a specific corresponding cell, such as the cell 1194.

Each output channel 1140a-n includes an integrated pump 1170a-n and a corresponding nozzle 1172a-n to facilitate flow of particles through the output channels 1140a-n. Additionally, at least some output channels 1140a-n are provided with corresponding reservoirs 1199a, 1199b. In the example illustrated in FIG. 11, one reservoir 1199a is provided for the output channel 1140a with the cell analysis portion 1190. The output from the remaining output channels 1140b-n is directed to a common reservoir 1199b for collection of waste, for example.

Thus, the example systems described above provide an efficient, cost-effective and user-friendly system for separation and analysis of various particles. Various examples include an integrated system which includes pumping, separation and analysis of various particles, such as cells, resulting in significant advantages, such as elimination of transfer of particles from one system to another and elimination of additional external components such as pumps.

The foregoing description of various examples has been presented for purposes of illustration and description. The foregoing description is not intended to be exhaustive or limiting to the examples disclosed, and modifications and variations are possible in light of the above teachings or may be acquired from practice of various examples. The examples discussed herein were chosen and described in order to explain the principles and the nature of various examples of the present disclosure and its practical application to enable one skilled in the art to utilize the present disclosure in various examples and with various modifications as are suited to the particular use contemplated. The features of the examples described herein may be combined in all possible combinations of methods, apparatus, modules, systems, and computer program products.

It is also noted herein that while the above describes examples, these descriptions should not be viewed in a limiting sense. Rather, there are several variations and modifications which may be made without departing from the scope as defined in the appended claims.

What is claimed is:

1. A system, comprising:
   an input channel having a first end and a second end to receive particles through the first end;
   a separation chamber in fluid communication with the second end of the input channel, the separation chamber having a passive separation structure, the passive separation structure including an array of columns spaced apart to facilitate separation of particles in a flow into at least two flow paths based on a size of the particles, wherein the size associated with a first flow path of the at least two flow paths corresponds to a cell;
   at least two output channels, each output channel coupled to the separation chamber to receive separated particles, wherein a first output channel is to receive the first flow path corresponding to a cell;
   an integrated pump configured to facilitate flow through the separation chamber, the integrated pump being positioned disposed entirely within an inside of at least one of the input channel or one of the at least two output channels; and
   a cell analysis portion coupled to the first output channel, the cell analysis portion being to perform at least one analysis associated with cells in the first output channel.

2. The system of claim 1, wherein the array of columns is arranged to deterministically direct a particle in a flow colliding with the columns to a first side if the particle in the flow is smaller than a critical diameter and to a second side if the particle in the flow is larger than the critical diameter.

3. The system of claim 1, wherein the integrated pump is an inertial pump.

4. The system of claim 1, wherein the integrated pump is a drop ejector.

5. The system of claim 1, wherein the integrated pump includes a thermal inkjet resistor or a piezo element.

6. The system of claim 1, further comprising a cell lysis portion to lyse cells in the first output channel.

7. The system of claim 6, further comprising:
   a reagent input channel in fluid communication with the first output channel, wherein flow from the reagent input channel is to mix with flow of separated particles from the separation chamber in the first output channel, the flow from the reagent input channel including a lysing agent.

8. The system of claim 6, further comprising:
   a detection portion to detect hybridization of biological material from the lysed cells.

9. The system of claim 8, further comprising:
   a biological material amplification portion to amplify biological material from the lysed cells, the biological material amplification portion being positioned to receive biological material from the cell lysis portion and to provide the amplified biological material to the detection portion.

10. The system of claim 6, further comprising:
    a biological material amplification portion to amplify biological material from the lysed cells;
    a sequencing portion to obtain a genetic sequence from the amplified biological material; and
    a mapping portion to identify a condition based on the genetic sequence.

11. The system of claim 10, wherein the mapping portion includes a machine learning portion to facilitate identification of condition using pattern matching.

12. The system of claim 1, wherein the cell analysis portion includes an antibody matching portion, the antibody matching portion including an array of cell identification regions, each cell identification region including antibodies to bind to a corresponding cell.

13. A system, comprising:
    an input channel to flow particles therethrough;
    a cell separation chamber in fluid communication with the input channel, the cell separation chamber including an array of columns spaced apart to facilitate separation of particles in a flow into at least two flow paths based on a size of the particles, wherein the size associated with a first flow path of the at least two flow paths corresponds to cell-sized particles;
    at least two output channels, each output channel coupled to the separation chamber to receive separated particles, wherein a first output channel is to receive the first flow path corresponding to the cell-sized particles;
    a cell lysing portion to mix a lysing agent with the cell-sized particles, the lysing agent to release biological material from cells;
    an integrated pump configured to facilitate flow through the separation chamber, the integrated pump being disposed entirely within an inside of at least one of the input channel or one of the at least two output channels; and
    a cell analysis portion to receive biological material from lysed cells, the cell analysis portion including at least one detection portion to identify a characteristic of the biological material.

14. The system of claim 1, wherein the cell lysing portion includes a reagent input channel in fluid communication with the first output channel.

15. A system, comprising:
- an input channel to flow particles therethrough;
- a cell separation chamber in fluid communication with the input channel, the cell separation chamber including an array of columns spaced apart to facilitate separation of particles in a flow into at least two flow paths based on a size of the particles, wherein the size associated with a first flow path of the at least two flow paths corresponds to cell-sized particles;
- at least two output channels, each output channel coupled to the separation chamber to receive separated particles, wherein a first output channel is to receive the first flow path corresponding to the cell-sized particles;
- a cell lysing portion to mix a lysing agent with the cell-sized particles, the lysing agent to release biological material from cells;
- an integrated pump configured to facilitate flow through the separation chamber, the integrated pump being disposed entirely within an inside of at least one of the input channel or one of the at least two output channels; and
- a biological material amplification portion to amplify biological material from lysed cells.

\* \* \* \* \*